United States Patent [19]

Nakaoku et al.

[11] Patent Number: 4,876,345

[45] Date of Patent: Oct. 24, 1989

[54] INDENE COMPOUNDS

[75] Inventors: Shozo Nakaoku; Kazuhiko Sakuma, both of Takayama; Yasuhiro Oshika, Sagamihara; Kazuo Ohira, Takayama, all of Japan

[73] Assignee: Taiyo Pharmaceutical Industry Co., Ltd., Takayama, Japan

[21] Appl. No.: 202,597

[22] Filed: Jun. 6, 1988

Related U.S. Application Data

[62] Division of Ser. No. 884,659, Jul. 11, 1986, Pat. No. 4,762,927.

[30] Foreign Application Priority Data

Feb. 3, 1986 [JP] Japan ................................. 61-21732

[51] Int. Cl.[4] .......................................... C07D 405/06
[52] U.S. Cl. ..................................... 544/379; 544/357; 544/364; 544/380; 546/187; 546/191; 548/305; 549/359; 549/433; 564/428
[58] Field of Search ................. 564/428; 549/359, 433; 548/305; 446/187; 546/191; 544/357, 364, 379, 380

[56] References Cited

U.S. PATENT DOCUMENTS

| | | | |
|---|---|---|---|
| 4,096,173 | 6/1978 | Molloy | 564/428 |
| 4,542,153 | 9/1985 | Witiak et al. | 514/466 |
| 4,723,022 | 2/1988 | Givens et al. | 564/428 |

OTHER PUBLICATIONS

Witiak et al. (II), "Chemical Abstracts", vol. 81, 1974, col. 3800u.

Rahwan et al., "Chemical Abstracts", vol. 87, 1977, col. 87:142u.
Witiak et al. (III), "Chemical Abstracts", vol. 90, 1979, col. 90:48256y.
Piascik et al., "Chemical Abstracts", vol. 91, 1979, col. 91:101925q.
Nakaoku et al., "Chemical Abstracts", vol. 107, 1987, col. 107:236253p.

*Primary Examiner*—Glennon H. Hollrah
*Assistant Examiner*—James H. Turnipseed
*Attorney Agent, or Firm*—Oblon, Spivakg, McClelland, Maier & Neustadt

[57] ABSTRACT

The invention provides an indene compound represented by the following general formula (I):

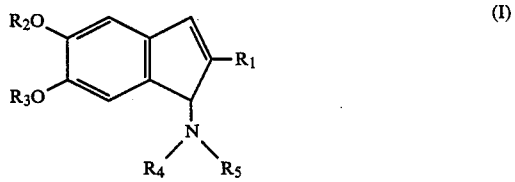

wherein $R_1$ means a lower alkyl group, $R_2$ and $R_3$ denote a lower alkyl group individually or an alkylenedioxy group in combination, and $R_4$ and $R_5$ mean individually a substituted or unsubstituted lower alkyl or aryl group or in combination a substituted or unsubstituted piperidino, piperazinyl or homopiperazinyl group together with the adjacent nitrogen atom, with a proviso that not both $R_4$ and $R_5$ are a methyl group at the same time.

16 Claims, No Drawings

INDENE COMPOUNDS

This is a division of application Ser. No. 884,649 filed July 11, 1986 now U.S. Pat. No. 4,762,927.

BACKGROUND OF THE INVENTION

1. Field of the Invention

This invention relates to indene compounds, and more specifically to indene compounds represented by the following general formula (I):

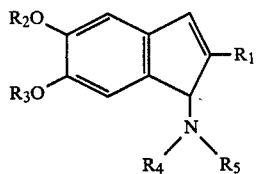

wherein $R_1$ means a lower alkyl group, $R_2$ and $R_3$ denote a lower alkyl group individually or an alkylenedioxy group in combination, and $R_4$ and $R_5$ mean individually a substituted or unsubstituted lower alkyl or aryl group or in combination a substituted or unsubstituted piperidino, piperazinyl or homopiperazinyl group together with the adjacent nitrogen atom, with a proviso that not both $R_4$ and $R_5$ are a methyl group at the same time.

2. Description of the Prior Art

As indene compounds, 2,3-substituted-5,6-methylenedioxyindenes have already been disclosed in U.S. Pat. No. 4,393,226. They have however been found dissatisfactory in the increasing effects of coronary blood flow.

SUMMARY OF THE INVENTION

An object of this invention is to provide novel indene compounds which are useful as therapeutic agents for angina pectoris and the like.

The present inventors have carried out a variety of investigations on indene compounds. As a result, it has been found that the above novel compounds represented by the general formula (I) are excellent in the increasing effects of coronary blood flow, antagonism of intracellular Ca, etc., leading to completion of this invention.

In one aspect of this invention, there is thus provided an indene compound represented by the following general formula (I):

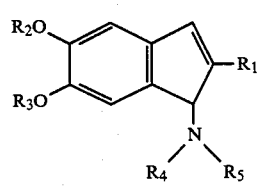

wherein $R_1$ means a lower alkyl group, $R_2$ and $R_3$ denote a lower alkyl group individually or an alkylenedioxy group in combination, and $R_4$ and $R_5$ mean individually a substituted or unsubstituted lower alkyl or aryl group or in combination a substituted or unsubstituted piperidino, piperazinyl or homopiperazinyl group together with the adjacent nitrogen atom, with a proviso that not both $R_4$ and $R_5$ are a methyl group at the same time.

The indene compounds (I) of this invention have strong increasing effects of coronary blood flow, and are hence useful as therapeutic agents for angina pectoris.

The above and other objects, features and advantages of the present invention will become apparent from the following description and appended claim.

DETAILED DESCRIPTION OF THE INVENTION AND PREFERRED EMBODIMENTS

In the compounds (I) of this invention, as substituent groups for the lower alkyl groups represented by $R_4$ and $R_5$, may for example be mentioned substituted or unsubstituted aryl groups, hydroxyl group, di(lower alkyl)amino groups, substituted or unsubstituted piperazinyl groups, piperidino group, etc. Illustrative examples of substituent groups for the piperidino group, piperazinyl group and homopiperazinyl group represented by $R_4$ and $R_5$ may include substituted or unsubstituted benzyl groups, aryl groups, lower alkyl groups, hydroxy lower alkyl groups, substituted or unsubstituted phenylcarbonyl groups and so on.

It should be borne in mind that the present invention embraces all isomers of the compounds represented by the general formula (I).

The indene compounds of this invention may be prepared, for example, by reacting an indene compound (III) with a secondary amine (II) in accordance with the following reaction formula:

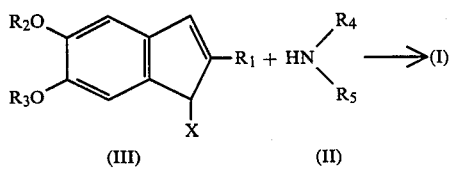

wherein X means a halogen atom and $R_1$, $R_2$, $R_3$, $R_4$ and $R_5$ have the same meaning as defined above.

The above reaction may be carried out by stirring the reactants at room temperature or under ice cooling for several hours in a solvent such as dimethylsulfoxide.

The starting compound represented by the general formula (III) is also a novel compound prepared by the present inventors. It may be prepared, for example, in accordance with the following reaction scheme:

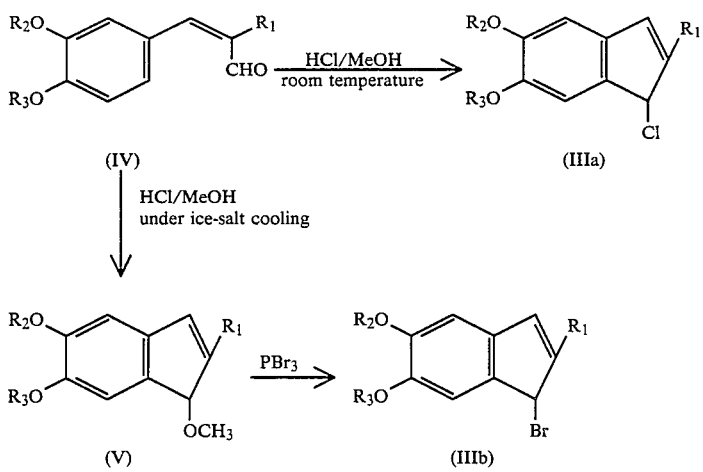

The compound (III) in which X is a chlorine atom, namely, the compound (IIIa) is obtained by bubbling hydrogen chloride gas at room temperature in a methanol solution of the compound represented by the general formula (IV), while the compound (III) in which X is a bromine atom, i.e., the compound (IIIb) is obtained by bubbling hydrogen chloride gas in the same methanol solution under ice-salt cooling to obtain the methoxy derivative (V) and then reacting the methoxy derivative (V) with phosphorus tribromide in chloroform as a solvent under ice cooling.

Among the secondary amines (II), the compounds in each of which $R_4$ means a lower alkyl group and $R_5$ denotes, for example, a substituted or unsubstituted lower alkyl group are novel compounds. These novel compounds include, for example, N-methyl-N-[4-[2-(1,3-benzothiazolyl)]benzyl]amine, N-methyl-N-[2-(4-isopropylthiophenyl)-2-hydroxyethyl]amine, N-methyl-N-[2-[4-(2-furanylcarbonyl)-1-piperazinyl]ethyl]amine, N-methyl-N-(2-piperidinoethyl)amine, N-methyl-N-[2-[4-[2-(4-isopropylthiophenyl)-2-hydroxyethyl]-1-piperazinyl]ethyl]amine. These novel compounds can be prepared, for example, in a manner which will later be described in detail in Referential Examples.

The thus-obtained indene compounds (I) of this invention may thereafter be converted, by conventional method, into their inorganic salts such as hydrochlorides, hydrobromides and hydroperchlorides and their organic salts such as fumarates, succinates, tartrates, maleates and oxalates, as needed.

[Effects]

The increasing effects of coronary blood flow and antagonism of intracellular Ca of the compounds (I) of this invention were tested by the following methods. Results are shown in Table 1.

(i) Increasing effects of coronary blood flow:

Their increasing effects of coronary blood flow were measured by the Langendorff method. After sacrificing each Hartley guinea pig having a body weight of approximately 250 g, its heart was removed promptly and then connected to a Langendorff's perfusion apparatus. Krebs-Henseleit solution (which contained 0.5% of defibrinated blood of guinea pig) gassed with 95%$O_2$+5%$CO_2$ at 25° C. was perfused to the heart through the aorta countercurrently. While guiding the effluent to a droplet counter to determine the number of droplets, each test compound at a concentration of $3 \times 10^{-4}$M dissolved in a physiological saline was perfused through an aortic cannula at a flow rate of 0.1 ml per 10 seconds. The change in the number of droplets induced by the test compound was determined at an interval of 1 minute. The rate of coronary vasodilation (%) was obtained through dividing the maximal value observed during 20 minutes after perfusing the test compound by the pretreatment value.

(ii) Antagonism of intracellular Ca:

The antagonism of intracellular Ca was measured by the Magnus method, using a herical strip of the thoracic aorta removed from each Wistar rat having a body weight of approximately 200 g. Namely, two strips of aorta specimens cut out from the same rat were thoroughly incubated under 1 g of resting load in a physiological salt solution (NaCl: 118 mM, KCl: 4.7 mM, $MgCl_2.6H_2O$: 0.54 mM, $NaH_2PO_4$: 1.0 mM, $NaHCO_3$: 25 mM, EDTA: 0.0027 mM, $CaCl_2.2H_2O$: 2.5 mM, and glucose: 2.5 mM) aerated with 95%$O_2$ +5%$CO_2$. After the equilibration period, the tissues were washed in a calcium-free physiological salt solution containing 1.0 mM EGTA and were equilibrated. After one aortic strip was contracted by the test compound of a concentration of $10^{-4}$ M in physiological saline and the other was contracted by the physiological saline, norepinephrine was added to both strips to give a final concentration of $3 \times 10^{-6}$ M. The tension developed by norepinephrine was recorded on a recorder through a force transducer and the phasic contraction Pd (control Ps) and tonic contraction Td (control Ts) were measured from its wave form.

Thereafter, two tissues were washed with the calcium-free nutrient solution, and they were again contracted by the same amount of norepinephrine to determine their respective contractile heights Hd (control Hs). Then, their intracellular Ca inhibitory effects (%) were calculated in accordance with the following equations.

Inhibition of phasic contraction
(%)=[1-(Pd/Hd)/(Ps/Hs)]×100

Inhibition of tonic contraction
(%)=[1-(Td/Hd)/(Ts/Hs)]×100

TABLE 1

| Compound* No. | Langerdorff method in guinea pig ($3 \times 10^{-4}$ M) Increase of coronary blood flow (%) | Intracellular Ca antagonism ($10^{-4}$ M) | |
|---|---|---|---|
| | | Phasic inhibition (%) | Tonic inhibition (%) |
| 5b | 46.1 | | |
| 8b | 18.8 | 56.6 | 57.1 |
| 12b | 29.7 | 76.6 | 63.0 |
| 13b | 19.9 | | |
| 14b | 29.8 | | |
| 15b | 24.2 | | |
| 16b | 45.7 | | |
| 17b | 89.4 | 60.7 | 54.0 |
| 18b | 70.0 | 43.4 | 8.8 |
| 19b | 42.3 | 39.4 | 36.6 |
| 20b | 53.5 | 71.5 | 1.8 |
| 21b | 45.1 | | |
| 22b | 30.3 | | |
| 23b | 28.3 | | |
| 24b | 34.3 | | |
| 25b | 39.5 | | |
| 26b | 65.9 | | |
| 27b | 108.8 | | |
| Control** | 17.1 | 20.9 | 61.1 |

*Indicated by Example number.
**2-n-Butyl-3-dimethylamino-5,6-methylenedioxyindene hydrochloride.

Having generally described this invention, a further understanding can be obtained by reference to certain specific examples which are provided herein for purpose of illustration only and are not intended to be limiting unless otherwise specified.

[Examples]

The present invention will hereinafter be described further by the following Referential Examples and Examples:

REFERENTIAL EXAMPLE 1:

Synthesis of 2-n-butyl-3-chloro-5,6-methylenedioxyindene

Dissolved in 1 ml of methanol was 114 mg of 2-n-butyl-3-(3,4-methylenedioxyphenyl)acrylaldehyde, into which hydrogen chloride gas was bubbled at room temperature for 5 minutes. The methanol was distilled off under reduced pressure, and the residue was purified by column chromatography on silica gel (eluent: a 10:1 mixture of n-hexane and ethyl acetate) to give 35 mg of 2-n-butyl-3-chloro-5,6-methylenedioxyindene having a melting point of 126°–128° C. as crystals (yield: 29%).

IR $\nu_{max}^{KBr}$cm$^{-1}$: 1470, 1325, 1030, 860, 710.

REFERENTIAL EXAMPLE 2:

Synthesis of 2-n-butyl-3-bromo-5,6-methylenedioxyindene (1) 2-n-Butyl-3-methoxy-5,6-methylenedioxyindene:

Dissolved in 80 ml of methanol was 12 g of 2-n-butyl-3-(3,4-methylenedioxyphenyl)acrylaldehyde, into which hydrogen chloride gas was blown under ice-salt cooling. Upon confirmation of full consumption of the raw material by thin-layer chromatography (eluent: a 5:1 mixture of n-hexane and ether), the bubbling of hydrogen chloride gas was stopped. Water was added to the reaction mixture, followed by extraction of the resultant mixture, followed by extraction of the resultant mixture with ether. After the resultant ether solution was washed with water, a saturated aqueous solution of sodium hydrogencarbonate and water successively, the ether solution was dried over anhydrous magnesium sulfate and then concentrated under reduced pressure. The residue was purified by column chromatography on silica gel (eluent: a 10:1 mixture of n-hexane and ether) to give 11.4 g of 2-n-butyl-3-methoxy-5,6-methylenedioxyindene as an oily substance (yield: 90%).

IR $\nu_{max}^{neat}$cm$^{-1}$: 1465, 1330, 1085, 1035.

(2) 2-n-Butyl-3-bromo-5,6-methylenedioxyindene:

Dissolved in 100 ml of chloroform was 9.3 g of 2-n-butyl-3-methoxy-5,6-methylenedioxyindene, followed by a dropwise addition of 15.4 g of phosphorus tribromide over 1 hour under ice cooling. After stirring the resultant mixture for further 4 hours, the reaction mixture was stirred for additional 4 hours at room temperature. The reaction mixture was washed with water, a 5% aqueous solution of sodium hydroxide and water successively, dried over anhydrous magnesium sulfate, and then concentrated under reduced pressure. The residue was purified by column chromatography on silica gel (eluent: a 20:1 mixture of n-hexane and ether) to give 7.6 g of 2-n-butyl-3-bromo-5,6-methylenedioxyindene having a melting point of 63.0°–64.0° C. as crystals (yield: 68%).

IR $\nu_{max}^{KBr}$cm$^{-1}$: 1470, 1330, 1038, 650.

REFERENTIAL EXAMPLE 3:

Following the procedure of Referential Example 2 except for the use of 2-n-propyl-3-(3,4-methylenedioxyphenyl)acrylaldehyde in place of the 2-n-butyl-3-(3,4-methylenedioxyphenyl)acrylaldehyde, was obtained 2-n-propyl-3-bromo-5,6-methylenedioxyindene having a melting point of 96°–97° C. as crystals.

IR $\nu_{max}^{KBr}$cm$^{-1}$: 1465, 1320, 1235, 1030, 860.

REFERENTIAL EXAMPLE 4:

Synthesis of N-methyl-N-[4-[2-(1,3-benzothiazolyl)]benzyl]amine (1) 2-(4-Bromomethylphenyl)-1,3-benzothiazole:

Refluxed for 1 hour was 150 ml of a carbon tetrachloride solution which contained 10 g of 2-(4-methylphenyl)-1,3-benzothiazole, 8.0 g of N-bromosuccinimide (NBS) and 0.2 g of benzoyl peroxide. After allowing the reaction mixture to cool down, the insoluble material was filtered off and the filtrate was concentrated under reduced pressure. The residue was recrystallized from ethanol to give 8.0 g of colorless crystals having a melting point of 128°–130° C. (yield: 59%).

IR $\nu_{max}^{KBr}$cm$^{-1}$: 1475, 1220, 965, 755, 600.

(2) N-Methyl-N-[4-[2-(1,3-benzothiazolyl)]benzyl]amine:

To a liquid mixture consisting of 150 ml of a 25% aqueous methylamine solution and 300 ml of tetrahydrofuran (THF), 7.2 g of 2-(4-bromomethylphenyl)-1,3-benzothiazole was added under ice cooling. The resulting mixture was stirred for 1.5 hours. Thereafter, a saturated aqueous solution of sodium chloride was added. The reaction mixture was extracted with ethyl acetate. After washing the ethyl acetate solution over water, the ethyl acetate solution was dried over anhydrous magnesium sulfate (MgSO$_4$) and then concentrated under reduced pressure. The residue was purified by column chromatography on silica gel (eluent: a 10:1 mixture of chloroform and methanol) to give 5.0 g of crystals having a melting point of 75°–77° C. (yield: 83%).

REFERENTIAL EXAMPLE 5:

Synthesis of N-methyl-N-[2-(4-isopropylthiophenyl)-2-hydroxyethyl]amine (1) Isopropylthiobenzene:

To a solution containing 75 g of thiophenol in 500 ml of dimethylformamide, 94 g of potassium carbonate was added under ice cooling and the resulting mixture was stirred for 30 minutes. Thereafter, 126 g of isopropyl bromide was added dropwise over 1 hour. The reaction mixture was then stirred overnight at room temperature. The insoluble material was filtered off. The filtrate was poured into water, extracted with ether, and then washed with a dilute aqueous solution of sodium hydrogencarbonate and water successively. The ether solution was dried over anhydrous magnesium sulfate, followed by its concentration under reduced pressure to give 102 g of residue. The reaction product was provided for the next reaction in its unpurified form.

IR $\nu_{max}^{neat}$cm$^{-1}$:2950, 1578, 1470, 1235, 735, 685.

(2) 4-Isopropylthioacetophenone:

To a solution containing 165 g of anhydrous stannic chloride in 200 ml of dichloromethane, 50 g of acetyl chloride was added dropwise over 10 minutes under ice cooling. After stirring the resulting mixture at the same temperature for 20 minutes, a solution of 88 g of isopropylthiobenzene in 200 ml of dichloromethane was added dropwise over 30 minutes. After stirring the reaction mixture at the same temperature for 1 hour and then at room temperature for 30 minutes, it was poured into ice water. The dichloromethane layer was washed with water, dried over anhydrous magnesium sulfate and then concentrated under reduced pressure. The residue was distilled under reduced pressure to obtain 36.9 g of a fraction at 122° C./0.4 Torr (yield: 33%).

IR $\nu_{max}^{neat}$cm$^{-1}$:2960, 1670, 1585, 1265, 1095, 820.

(3) 4-Isopropylthio-α-bromoacetophenone:

To a solution containing 36.9 g of 4-isopropylthioacetophenone and 1 ml of 48% hydrobromic acid in 330 ml of acetic acid, a solution of 30.3 g of bromine in 20 ml of acetic acid was added dropwise over 1 hour at 10° C. After adding ether and then washing the resultant mixture with water, a saturated aqueous solution of sodium hydrogencarbonate, an aqueous solution of sodium thiosulfate and water successively, the ethereal layer was dried over anhydrous magnesium sulfate and then concentrated under reduced pressure. The residue was recrystallized from ethanol to give 40 g of crystals having a melting point of 54°–56° C. (yield: 77%).

IR $\nu_{max}^{KBr}$cm$^{-1}$:2960, 1685, 1585, 1085, 805.

(4) 4-Isopropylthiophenyloxirane:

Added at room temperature to a solution of 1.23 g of 4-isopropylthio-α-bromoacetophenone in 15 ml of methanol was 170 mg of sodium boron hydride, followed by stirring of the resulting mixture for 15 minutes. After adding ether to the reaction mixture and then washing it with water, the mixture was dried over anhydrous sodium sulfate and concentrated under reduced pressure. The residue was dissolved in 20 ml of THF, to which 20 ml of a 3% aqueous solution of sodium hydroxide was added at room temperature. The thusprepared mixture was stirred for 15 minutes. The mixture was extracted with ether, washed with water, dried over anhydrous magnesium sulfate, and then concentrated under reduced pressure to give 1.0 g of an oily substance. The reaction product was provided for the next reaction in its unpurified form. NMR(CDCl$_3$) δ:

$$1.24\ (6H,\ d,\ J=6Hz\ -\!\!\!<\!\!{}^{CH_3}_{CH_3})\ 2.72-3.18\ (2H,\ m,$$

$$CH_2\!\!-\!\!\!\!\overset{\displaystyle\diagdown}{\underset{O}{\diagup}}),$$

3.36 (1H, m, J=6Hz —CH<), 3.76–3.86 (1H, m, CH-Ph), 7.12–7.40(4H, arom.).

(5) N-Methyl-N-[2-(4-isopropylthiophenyl)-2-hydroxyethyl]amine:

A solution of 842 mg of 4-isopropylthiophenyloxirane in 30 ml of methanol which contained 20% of methylamine was reacted at 70° C. in a sealed tube for 41 hours. After allowing the reaction mixture to cool down, the reaction mixture was concentrated under reduced pressure and the residue was purified by column chromatography on silica gel (eluent: a 10:1 mixture of chloroform and methanol) to give 428 mg of an oily substance.

NMR(CDCl$_3$) δ:

$$1.30\ (6H,\ d,\ J=7Hz\ -\!\!\!<\!\!{}^{CH_3}_{CH_3})$$

2.48 (3H, s, CH$_3$—N), 2.74–3.86 (2H, m, CH$_2$—N), 3.16–3.36 (2H, NH, OH), 3.40 (1H, m, J=7Hz, —CH<), 4.74–4.90 (1H, m, CH—Ph), 7.30–7.60 (4H, arom.).

REFERENTIAL EXAMPLE 6:

Synthesis of N-methyl-N-[2-(4-(2-furanylcarbonyl)-1-piperazinyl)ethyl]amine (1) 1-(2-Furanylcarbonyl)-4-[2-(2-furanylcarbonyloxy)ethyl]piperazine:

To a solution of 12.5 g of 1-piperazine ethanol and 23.7 g of triethylamine in 200 ml of benzene, a solution of 22.6 g of 2-furancarbonyl chloride in 50 ml of benzene was gradually added dropwise under ice cooling. After the addition, the reaction mixture was stirred for further 2 hours. It was then washed with a saturated aqueous solution of sodium hydrogencarbonate and water successively, dried over anhydrous magnesium sulfate and then concentrated under reduced pressure to give 25.2 g of an oily substance. The reaction product was provided for the next step in its unpurified form.

NMR(CDCl$_3$) δ:

$$2.56-2.72\ (4H,\ CHN\!\!<\!\!{}^{CH_2}_{CH_2}),$$

2.80 (2H, t, J=6Hz, CH$_2$N<), 3.76–3.90 (4H, CO—N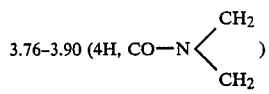)

4.46 (2H, t, J=6Hz, CH₂O—), 6.46–7.66 (6H, arom.).

(2)
1-(2-Furanylcarbonyl)-4-(2-hydroxyethyl)piperazine:

To a solution of 3.7 g of 1-(2-furanylcarbonyl)-4-(2-(2-furanylcarbonyloxy)ethyl)piperazine in 30 ml of methanol, 12.5 ml of a 3% aqueous solution of sodium hydroxide was added at room temperature. The resulting mixture was stirred for 40 minutes. After distilling off the methanol under reduced pressure, the residue was taken up in chloroform and then washed once with a saturated aqueous solution of sodium chloride. The chloroform layer was dried over anhydrous magnesium sulfate and then concentrated under reduced pressure. The residue was purified by column chromatography on silica gel (eluent: a 10:1 mixture of chloroform and methanol) to give 2.3 g of an oily substance (yield: 82%).

NMR(CDCl₃) δ:

2.52–2.92 (7H, CH₂N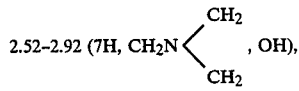, OH), 3.68 (2H, t, J=6Hz, OCH₂), 3.76–3.92 (4H, CON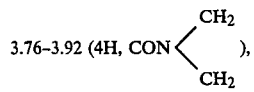), 6.48–7.54(3H, arom.).

(3) 1-(2-Furanylcarbonyl)-4-(2-chloroethyl)piperazine:

Dissolved in 20 ml of thionyl chloride was 1.76 g of 1-(2-furanylcarbonyl)-4-(2-hydroxyethyl)piperazine. The resulting mixture was stirred at room temperature for 7.5 hours. The thionyl chloride was distilled off under reduced pressure and the residue was poured into cold water. After alkalinization of the resulting aqueous solution with sodium carbonate, the solution was extracted with benzene and the benzene layer was washed with water. The benzene layer was dried over anhydrous magnesium sulfate and thereafter concentrated under reduced pressure to give 1.2 g of an oily substance. The reaction product was provided for the next step in its unpurified form.

IRν$_{max}^{neat}$cm⁻¹:2800, 1610, 1560, 1420, 1260, 1000, 750.

(4)
N-Methyl-N-[2-(4-(2-furanylcarbonyl)-1-piperazinyl)ethyl]amine:

A solution of 1.0 g of 1-(2-furanylcarbonyl)-4-(2-chloroethyl)piperazine and 200 mg of sodium iodide in 40 ml of methanol which contained 25% of methylamine was reacted at 70° C. in a sealed tube for 24 hours. After allowing the reaction mixture to cool down, the reaction mixture was concentrated under reduced pressure and the residue was purified by column chromatography on silica gel (eluent: a 20:1:0.1 mixture of chloroform, methanol, and methanol containing 40% methylamine) to give 800 mg of crystals (yield: 82%).

IR ν$_{max}^{neat}$cm⁻¹:2940, 2800, 1610, 1560, 1430, 1010, 760.

REFERENTIAL EXAMPLE 7:

Synthesis of N-methyl-N-(2-piperidinoethyl)amine

A solution of 8.0 g of N-(2-chloroethyl)piperidine hydrochloride and 0.5 g of sodium iodide in 60 ml of methanol which contained 40% of methylamine was reacted at 70° C. in a sealed tube for 20 hours. After allowing the reaction mixture to cool down, the reaction mixture was concentrated under reduced pressure. The residue was added with ether, followed by a further addition of 10 g of ground sodium hydroxide. The resulting mixture was stirred for 2 hours. The insoluble material was filtered off and the filtrate was concentrated under the atmospheric pressure. The residue was distilled under reduced pressure to give 4.5 g of a fraction at 80° C./18 Torr (yield: 73%).

NMR(CDCl₃) δ:

1.30–1.76 (6H, N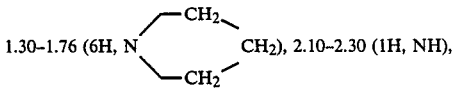CH₂), 2.10–2.30 (1H, NH), 2.36–2.76 (8H, CH₂CH₂N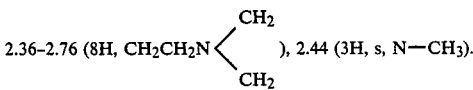), 2.44 (3H, s, N—CH₃).

REFERENTIAL EXAMPLE 8:

Synthesis of N-methyl-N-[2-[4-[2-(4-isopropylthiophenyl)-2-hydroxyethyl)]-1-piperazinyl]ethyl]amine (1)
4-Isopropylthio-α-[4-(2-hydroxylethyl)-1-piperazinyl]acetophenone:

To a solution containing 3.6 g of 1-piperazine ethanol and 3.9 g of sodium carbonate in 30 ml of dimethylsulfoxide, a solution of 5.0 g of 4-isopropylthio-α-bromacetophenone in 20 ml of dimethylsulfoxide was gradually added dropwise under ice cooling. After the addition, the reaction mixture was stirred at room temperature for 1 hour, added with a saturated aqueous solution of sodium chloride and then extracted with chloroform. The chloroform layer was washed once with a saturated aqueous solution of sodium chloride. After drying the chloroform layer over anhydrous magnesium sulfate, it was concentrated under reduced pressure and the residue was purified by column chromatography on silica gel (eluent: a 10:1 mixture of chloroform and methanol) to give 4.8 g of crystals (yield: 81%).

IR [$_{max}^{KBr}$cm⁻¹:3400, 2940, 2820, 1680, 1590, 1165, 975.

(2)
4-Isopropylthio-α-[4-(2-chloroethyl)-1-piperazinyl]acetophenone:

After stirring a solution of 4.8 g of 4-isopropylthio-α-[4-(2-hydroxyethyl)-1-piperazinyl]acetophenone in 40 ml of thionyl chloride for 4 hours under ice cooling, the solution was concentrated under reduced pressure. Ice water was added to the residue, the resulting mixture made alkaline with sodium carbonate and then extracted with ethyl acetate. After washing the ethyl acetate layer with water, it was dried over anhydrous magnesium sulfate and concentrated under reduced pressure. The residue was purified by column chromatography on silica gel (eluent: a 15:1 mixture of chloroform and acetone) to give 2.3 g of crystals (yield: 45%). Since the reaction product was unstable, it was immediately provided for the next step.

IR $\nu_{max}^{KBr}$cm$^{-1}$:2930, 2800, 1670, 1580, 1215, 1090, 970, 815.

(3)
4-Isopropylthio-α-[4-(2-(N-methylamino)ethyl)-1-piperazinyl]acetophenone:

A solution of 3.45 g of 4-isopropylthio-α-[4-(2-chloroethyl)-1-piperazinyl]acetophenone and 0.5 g of potassium iodide in 50 ml of methanol which contained 20% of methylamine was reacted at 60° C. in a sealed tube for 10 hours. After allowing the reaction mixture to cool down, it was purified by column chromatography on silica gel (eluent: a 5:1:0.1 mixture of chloroform, methanol, and methanol containing 40% of methylamine) to give 2.5 g of an oily substance (yield: 74%).

IR $\nu_{max}^{neat}$cm$^{-1}$:3300, 2925, 2800, 1665, 1585, 1440, 1150, 750.

(4)
N-Methyl-N-[2-(4-(2-(4-isopropylthiophenyl)-2-hydroxyethyl)-1-piperazinyl)ethyl]amine:

After gradually adding 0.5 g of sodium boron hydride to 4.0 g of 4-isopropylthio-α-[4-(2-(N-methylamino)ethyl)-1-piperazinyl]acetophenone in 50 ml of methanol under ice cooling, the resulting mixture was stirred for 1.5 hours. It was concentrated under reduced pressure and the residue was purified by column chromatography on silica gel (eluent: a 5:1:0.1 mixture of chloroform, methanol, and methanol containing 40% of methylamine) to give 3.1 g of an oily substance (yield: 77%).

IR $\nu_{max}^{neat}$cm$^{-1}$:3100, 2920, 2800, 1440, 1150, 820.

As other secondary amines which are employed in subsequent Examples, commercial products or those synthesized by known processes were used.

EXAMPLE 1:

Synthesis of 2-n-butyl-3-diethylamino-5,6-methylenedioxyindene

To a solution containing 300 mg of diethylamine and 430 mg of sodium carbonate in 6 ml of dimethylsulfoxide, 600 mg of 2-n-butyl-3-bromo-5,6-methylenedioxyindene was added at room temperature. The reaction mixture was stirred for 5 hours. After completion of the reaction, the reaction mixture was added with a saturated aqueous solution of sodium hydrogencarbonate and then extracted with ether. The ethereal layer was washed with water, dried over anhydrous magnesium sulfate and then concentrated under reduced pressure. The residue was purified by column chromatography on silica gel (eluent: a 10:1 mixture of n-hexane and ether) to give 380 mg of an oily substance (yield: 65%).

NMR(CDCl$_3$) δ: .88–1.04 (3H, m, —CH$_3$), 1.08 (6H, t, J=8Hz, N(CH$_2$CH$_3$)$_2$), 1.26–1.76 (4H, m, —CH$_2$CH$_2$—),

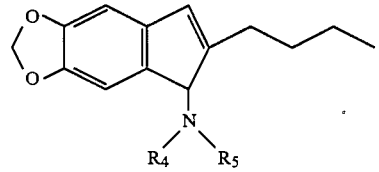

2.60 (4H, q, J=8Hz, N—(CH$_2$—CH$_3$)$_2$), 4.30 (1H, s, CH—N), 6.04 (2H, s, O—CH$_2$), 6.42 (1H, s, CH=C), 6.82 (1H, s, arom.), 7.14 (1H, s arom.).

IR $\nu_{max}^{neat}$cm$^{-1}$:2960, 1470, 1320, 1040.

The above compound was dissolved in ether, into which hydrogen chloride gas was then blown to convert it into its corresponding hydrochloride. Melting point: 139°–141.5° C..

IR $\nu_{max}^{KBr}$cm$^{-1}$:2920, 2670-2100, 1470, 1320, 1225, 1030, 930.

EXAMPLES 2–28:

Using the secondary amines shown in the Referential Examples and known secondary amines instead of diethylamine employed in Example 1, compounds shown in Table 2 were separately obtained in the same manner as in Example 1.

TABLE 2-1

[Structure with R$_4$, R$_5$ substituents on N]

| Example | R$_4$ | R$_5$ | Salt | Appearance | Yield (%) | m.p. (°C.) |
|---|---|---|---|---|---|---|
| 2a | CH$_3$ | n-Bu | | oily | 86 | |
| 2b | " | " | .HCl | crystalline | | 131–133 |
| 3a | CH$_3$ | 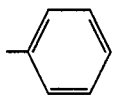 | | crystalline | 96 | 89.5–91.0 |

TABLE 2-1-continued

[Structure: methylenedioxy-fused indene with butyl substituent and NR₄R₅ group]

| Example | R₄ (Compound) | R₅ (Compound) | Salt | Appearance | Yield (%) | m.p. (°C.) |
|---|---|---|---|---|---|---|
| 4a | | piperidine (N-ring) | | crystalline | 94 | 54.5–56.5 |
| 4b | | " | .HCl | crystalline | | 191–193 (decomp'd) |
| 5a | | piperazine-CH₂-(2,3,4-trimethoxyphenyl) | | oily | 98 | |
| 5b | | " | .HCl | crystalline | | 188–190 (decomp'd) |
| 6a | CH₃ | —CH₂—(4-(benzothiazol-2-yl)phenyl) | | crystalline | 93 | 91–93 |
| 6b | " | " | .HCl | crystalline | | 191.5–192.5 |
| 7a | CH₃ | —CH₂CHOH—(4-(isopropylthio)phenyl) | | oily | 90 | |
| 7b | " | " | .HCl | crystalline | | 168–173 (decomp'd) |
| 8a | CH₃ | —CH₂CH₂—N(piperazine)N—CO-(2-furyl) | | oily | 76 | |
| 8b | " | " | .HCl | crystalline | | 145–152 (decomp'd) |
| 9a | CH₃ | —CH₂—phenyl | | oily | 98 | |
| 9b | " | " | .HCl | crystalline | | 174.0–175.5 |
| 10a | | piperazine-CH₂-phenyl | | oily | 85 | |
| 10b | | " | .HCl | crystalline | | 185–189 (decomp'd) |
| 11a | | piperazine-phenyl | | crystalline | 88 | 128–130 |
| 11b | | " | .HCl | crystalline | | 145–150 (decomp'd) |

TABLE 2-1-continued
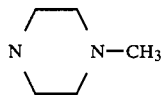
| Example | Compound R4 | R5 | Salt | Appearance | Yield (%) | m.p. (°C.) |
|---|---|---|---|---|---|---|
| 12a | | 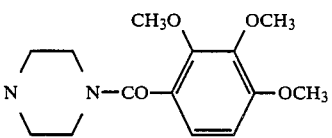 | | crystalline | 93 | 83–85 |
| 12b | | " | .HCl | crystalline | | 180–183 (decomp'd) |
| 13a | | 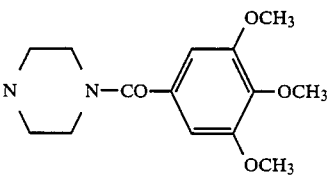 | | amorphous | 95 | |
| 13b | | " | .HCl | crystalline | | 118–122 |
| 14a | | 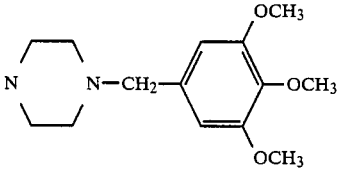 | | amorphous | 76 | |
| 14b | | " | .HCl | crystalline | | 120–125 |
| 15a | | 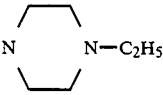 | | amorphous | 76 | |
| 15b | | " | .HCl | crystalline | | 150–155 |
| 16a | CH3 | —CH2CH2N(CH3)2 | | oily | 41 | |
| 16b | " | " | .HCl | crystalline | | 159–163 (decomp'd) |
| 17a | | 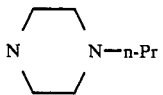 | | crystalline | 83 | 66.0–67.5 |
| 17b | | " | .HCl | crystalline | | 155.0–158.0 |
| 18a | | 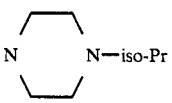 | | oily | 95 | |
| 18b | | " | .HCl | crystalline | | 149.0–152.0 |
| 19a | | N⏜N—iso-Pr | | oily | 85 | |
| 19b | | " | .HCl | crystalline | | 154.0–157.0 |

TABLE 2-1-continued

[Structure: methylenedioxy-fused indene with butyl substituent and NR4R5 group]

| Example | R4 | R5 | Salt | Appearance | Yield (%) | m.p. (°C.) |
|---|---|---|---|---|---|---|
| 20a | | N⌒N—CH₂CH₂OH | | crystalline | 81 | 82.0–84.0 |
| 20b | | " | .HCl | crystalline | | 155.0–158.0 |
| 21a | CH₃ | —CH₂CH₂CH₂N(CH₃)₂ | | oily | 55 | |
| 21b | " | " | .HCl | crystalline | | 168.0–171.0 |
| 22a | CH₃ | —CH₂CH₂N(C₂H₅)₂ | | oily | 66 | |
| 22b | " | " | .HCl | crystalline | | 120.0–124.0 |
| 23a | CH₃ | —CH₂CH₂—N(piperidine) | | oily | 64 | |
| 23b | " | " | .HCl | crystalline | | 116.0–120.0 |
| 24a | | N⌒N—iso-Bu | | oily | 80 | |
| 24b | | " | .HCl | crystalline | | 195–196 (decomp'd) |
| 25a | | N⌒N—C₂H₅ (homopiperazine) | | oily | 46 | |
| 25b | | " | .HCl | crystalline | | 155–160 |
| 26a | | N⌒N—n-Bu | | oily | 91 | |
| 26b | | " | .HCl | crystalline | | 177–180 (decomp'd) |
| 27a | CH₃ | —CH₂CH₂N⌒N—CH₂CH(OH)—C₆H₄—S—iso-Pr | | oily | 79 | |
| 27b | " | " | .HCl | crystalline | | 179–184 (decomp'd) |
| 28a | | N⌒N—C₂H₅ | | oily | 95 | |
| 28b | | " | .HCl | crystalline | | |

Note: In the compounds of Examples 28a and 28b, R₁ is a n-propyl group.
Note: The compound of Example 7a is a diastereomer. The hydrochlorides in Examples 7b, 27a and 27b are each a mixture of diastereomers.

TABLE 2-2

| Example | Compound (see, Table 2-1) | NMR (CDCl₃) δ | IR $\nu_{max}^{neat}$ or $KBr$ cm$^{-1}$ |
|---|---|---|---|
| 2a | | 0.84–1.04 (6H, m, —CH₃, —CH₃), 1.24–1.74 (8H, m, —CH₂CH₂—, —CH₂CH₂—), 2.14 (3H, s, N—CH₃), 2.35 (2H, t, J=8Hz, N—CH₂—), 2.58 (2H, t, J=8Hz, ⟩—CH₂—), 4.06 (1H, s, N—CH), 5.88 (2H, s, OCH₂—), 6.23 (1H, s, CH=C), 6.63 (1H, s, arom.), 6.92 (1H, s, arom.) | 2930, 1465, 1320, 1040 |
| 2b | .HCl | | 2950, 2700–2100, 1460, 1320, 1225, 1030, 930 |
| 3a | | 0.84–1.02 (3H, m, —CH₃), 1.26–1.76 (4H, m, —CH₂CH₂—), 2.32 (2H, t, J=8Hz, ⟩—CH₂—), 2.48 (3H, s, N—CH₃), 5.36 (1H, s, CH—N), 6.04 (2H, s, —OCH₂), 6.56 (1H, s, CH=C), 6.90–7.56 (7H, m, arom.) | 2920, 1590, 1495, 1465, 1320, 1030, |
| 4a | | 0.88–1.02 (3H, m, —CH₃), 1.18–1.74 (10H, m, —CH₂CH₂—, —N(CH₂CH₂)₂CH₂), 2.34 (2H, t, J=8Hz, ⟩—CH₂—), 2.40–2.70 (4H, m, —N(CH₂CH₂)), 3.96 (1H, s, CH—N), 5.86 (2H, s, OCH₂—), 6.22 (1H, s, CH=C), 6.62 (1H, s, arom.), 6.96 (1H, s, arom.) | 2920, 1460, 1310, 1040 |
| 4b | .HCl | | 2920, 2680–2100, 1470, 1330, 1030, 930 |
| 5a | | 0.84–1.04 (3H, m, —CH₃), 1.22–1.72 (4H, m, —CH₂CH₂—), 2.28–2.80 (10H, m, ⟩—CH₂—, N⟨⟩N—CH₂), 3.44 (2H, s, —CH₂—Ph), 3.84 (9H, s, (—OCH₃)₃), 4.02 (1H, s, CH—N), 5.88 (2H, s, —OCH₂—), 6.24 (1H, s, CH=C), 6.56–7.06 (4H, arom.) | 2925, 1595, 1460, 1290, 1090, 730 |
| 5b | .HCl | | 2920, 2680–2100, 1600, 1470, 1330, 1280, 1100, 1030 |
| 6a | | 0.84–1.02 (3H, m, —CH₃), 1.20–1.74 (4H, m, —CH₂CH₂—), 2.22 (3H, s, N—CH₃), 2.44 (2H, t, J=8Hz, ⟩—CH₂—), 3.68 (2H, s, N—CH₂—), 4.14 (1H, s, N—CH), 5.92 (2H, s, OCH₂—), 6.28 (1H, s, CH=C), 6.67 (1H, s, arom.), 7.05 (1H, s, arom.), 7.23–8.12 (8H, m, arom.) | 2920, 1460, 1310, 1035, 725 |
| 6b | .HCl | | 2920, 2700–2150, 1470, 1325, 1230, 1020 |
| 7a | (diastereomer) | 0.90–1.06 (3H, m, —CH₃), 1.26 (2H, d, J=8Hz, —CH(CH₃)CH₃), 1.20–1.74 (4H, m, —CH₂CH₂—), 2.22–2.86 (4H, m, ⟩—CH₂, N—CH₂—), 2.48 (3H, s, N—CH₃), 3.36 (1H, m, —CH), 4.10 (1H, brs, OH), 4.18 (1H, s, CH—N), 4.78 (1H, dd, J=4, 10Hz, CH—OH), 5.96 (2H, s, OCH₂—), 6.36 (1H, s, CH=C), 6.71 (1H, s, arom.), 7.05 (1H, s, arom.), 7.38–7.46 (4H, arom.) | 3400, 2950, 1460, 1320, 1035 |

TABLE 2-2-continued

| Example | Compound (see, Table 2-1) | NMR (CDCl₃) δ | IR $\nu_{max}^{neat\ or\ KBr}$ cm$^{-1}$ |
|---|---|---|---|
| | | 0.86–1.06 (3H, m, —CH₃), 1.28 (6H, d, J=8Hz, —CH(CH₃)₂), 1.20–1.74 (4H, m, —CH₂CH₂—), 2.08 (3H, s, N—CH₃), 2.42 (2H, t, J=8Hz, >—CH₂—), 2.70–3.22 (2H, m, N—CH₂—), 3.38 (1H, m, —CH<), 4.10 (1H, s, CH—N), 4.24 (1H, brs, OH), 4.74 (1H, dd, J=4,10Hz, C<u>H</u>—OH), 5.94 (2H, s, —OCH₂—), 6.36 (1H, s, CH=C), 6.72 (1H, s, arom.), 6.90 (1H, s, arom.), 7.32–7.52 (4H, arom.) | 3400, 2950, 1460, 1318, 1035 |
| 7b | (diastereomer mixture) .HCl | | 3330, 2950, 2730–2200, 1470, 1320, 1230, 1030 |
| 8a | | 0.86–1.06 (3H, m, —CH₃), 1.22–1.72 (4H, m, —CH₂CH₂—), 2.24–2.80 (10H, m, >—CH₂—, N—CH₂CH₂—N(CH₂CH₂)₂N—), 2.32 (3H, s, N—CH₃), 3.72–3.92 (4H, m, (CH₂CH₂)₂N—CO), 4.12 (1H, s, CH—N), 5.96 (2H, s, OCH₂—), 6.32 (1H, s, CH=C), 6.46–7.54 (5H, arom.) | 2920, 1615, 1460, 1280, 1030, 750 |
| 8b | .HCl | | 2920, 2720–2100, 1620, 1475, 1420, 1320, 1280, 1030 |
| 9a | | 0.84–1.04 (3H, m, —CH₃), 1.22–1.74 (4H, m, —CH₂CH₂—), 2.18 (3H, s, N—CH₃), 2.46 (2H, t, J=8Hz, >—CH₂), 3.69 (2H, s, CH₂—Ph), 4.16 (1H, s, CH—N), 5.94 (2H, s, OCH₂—), 6.30 (1H, s, CH=C), 6.69 (1H, s, arom.), 7.08 (1H, s, arom.), 7.20–7.46 (5H, m, arom.) | 2925, 1460, 1320, 1040, |
| 9b | .HCl | | 2920, 2720–2100, 1475, 1320, 1020, 925 |
| 10a | | 0.86–1.04 (3H, m, —CH₃), 1.22–1.72 (4H, m, —CH₂CH₂—), 2.22–2.82 (10H, m, >—CH₂—, N(CH₂CH₂)₂N), 3.46 (2H, s, CH₂—Ph), 4.02 (1H, s, CH—N), 5.88 (2H, s, OCH₂—), 6.26 (1H, s, CH=C), 6.66 (1H, s, arom.), 7.02 (1H, s, arom.), 7.26 (5H, s, arom.) | 2925, 1460, 1320, 1135, 1035 |
| 10b | .HCl | | 2920, 2720–2100, 1470, 1325, 1030, 925 |
| 11a | | 0.88–1.06 (3H, m, —CH₃), 1.24–1.76 (4H, m, —CH₂CH₂—), 2.46 (2H, t, J=8Hz, >—CH₂—), 2.70–3.28 (8H, m, N(CH₂CH₂)₂N), 4.20 (1H, s, CH—N), 6.02 (2H, s, OCH₂—), 6.44 (1H, s, CH=C), 6.82–7.48 (7H, arom.) | 2920, 1590, 1460, 1310, 1230, 1030, 750 |
| 11b | .HCl | | 2920, 2700–2100, 1590, 1470, 1330, 1030 |
| 12a | | 0.88–1.08 (3H, m, —CH₃), 1.22–1.76 (4H, m, —CH₂CH₂—), 2.22–2.88 (8H, m, N(CH₂CH₂)₂N), 2.32 (3H, s, N—CH₃), 4.15 (1H, s, CH—N), 6.02 (2H, s, OCH₂—), 6.22 (1H, s, CH=C), 6.80 (1H, s, arom.), 7.18 (1H, s, arom.) | 2925, 1470, 1320, 1145, 1035, 865 |
| 12b | .HCl | | 2920, 2700–2100, 1470, 1330, 1030 |

TABLE 2-2-continued

| Example | Compound (see, Table 2-1) | NMR (CDCl₃) δ | IR $\nu_{max}^{neat\ or\ KBr}$ cm⁻¹ |
|---|---|---|---|
| 13a | | 0.88–1.06 (3H, m, —CH₃), 1.22–1.72 (4H, m, —CH₂CH₂—), 2.20–2.90 (6H, m, $\rangle$—CH₂, C—N$\langle^{CH_2}_{CH_2}$ ), 3.24–3.90 (4H, m, CON$\langle^{CH_2}_{CH_2}$ ), 3.88–4.00 (9H, (OCH₃)₃), 4.14 (1H, s, CH—N), 6.02 (2H, s, OCH₂), 6.40 (1H, s, CH=C), 6.74–7.12 (4H, arom.) | 2925, 1620, 1480, 1280, 1095 |
| 13b | .HCl | | 2925, 2700–2100, 1620, 1460, 1410, 1280, 1090, 1030 |
| 14a | | 0.88–1.04 (3H, m, —CH₃), 1.24–1.72 (4H, m, —CH₂CH₂—), 2.42 (2H, t, J=8Hz, $\rangle$—CH₂—), 2.52–2.88 (4H, m, C—N$\langle^{CH_2-}_{CH_2-}$ ), 3.48–3.80 (4H, m, CON$\langle^{CH_2-}_{CH_2-}$ ), 3.90 (9H, s, (OCH₃)₃), 4.16 (1H, s, CH—N), 6.04 (2H, s, OCH₂—), 6.42 (1H, s, CH=C), 6.72 (2H, s, arom.), 6.78 (1H, s, arom.), 7.08 (1H, s, arom.) | 2925, 1625, 1580, 1460, 1325, 1125 |
| 14b | .HCl | | 2925, 2700–2100, 1625, 1590, 1460, 1410, 1325, 1230, 1110, 1030 |
| 15a | | 0.88–1.04 (3H, m, —CH₃), 1.24–1.72 (4H, m, —CH₂CH₂—), 2.28–2.84 (10H, m, $\rangle$—CH₂, N⌒N), 3.46 (2H, s, CH₂Ph), 3.88 (9H, s, (OCH₃)₃), 4.12 (1H, s, CH—N), 6.00 (2H, s, —OCH₂—), 6.36 (1H, s, CH=C), 6.66 (2H, s, arom.), 6.76 (1H, s, arom.), 7.14 (1H, s, arom.) | 2925, 1590, 1460, 1320, 1120, 750 |
| 15b | .HCl | | 2925, 2700–2100, 1590, 1460, 1410, 1330, 1240, 1120, 1030 |
| 16a | | 0.88–1.02 (3H, m, —CH₃), 1.24–1.76 (4H, m, —CH₂CH₂—), 2.26 (6H, s, N$\langle^{CH_3}_{CH_3}$ ), 2.30 (3H, s, $\rangle$—N—CH₃), 2.30–2.82 (6H, m, N—CH₂CH₂—N, $\rangle$—CH₂—), 4.16 (1H, s, CH—N), 6.00 (2H, s, OCH₂), 6.38 (1H, s, CH=C), 6.78 (1H, s, arom.), 7.12 (1H, s, arom.) | 2925, 1460, 1310, 1035, 750 |
| 16b | .HCl | | 2920, 2700–2100, 1470, 1320, 1030 |
| 17a | | 0.84–1.20 (6H, m, N—CH₂C$\underline{H}$₃, —CH₃), 1.22–1.78 (4H, m, —CH₂CH₂—), 2.24–2.90 (12H, m, $\rangle$—CH₂, —N⌒N—CH₂—), 4.10 (1H, s, CH—N), 6.00 (2H, s, —OCH₂—), 6.40 (1H, s, CH=C), 6.76 (1H, s, arom.), 7.16 (1H, s, arom.) | 2925, 1460, 1310, 1030, 860 |
| 17b | .HCl | | 2920, 2700–2100, 1475, 1330, 1030 |
| 18a | | 0.80–1.04 (6H, —CH₃, —CH₃), 1.18–1.74 (6H, m, —CH₂CH₂—, N—CH₂C$\underline{H}$₃), 2,18–2.88 (12H, m, $\rangle$—CH₂, N⌒N—CH₂—), 4.02 (1H, s, CH—N), 5.88 (2H, s, OCH₂), 6.26 (1H, s, CH=C), 6.64 (1H, s, arom.), 7.02 (1H, s. arom.) | 2925, 1460, 1320, 1150, 1035, 935, 850, 750 |
| 18b | .HCl | | 2925, 2700–2100, 1475, |

TABLE 2-2-continued

| Example | Compound (see, Table 2-1) | NMR (CDCl₃) δ | IR $\nu_{max}^{neat\ or\ KBr}$ cm$^{-1}$ |
|---|---|---|---|
| | | | 1330, 1030, 930 |
| 19a | | 0.88–1.00 (3H, m, —CH₃), 1.02 (6H, d, J=7Hz, —CH(CH₃)₂), 1.24–1.74 (4H, m, —CH₂CH₂—), 2.28–2.84 (11H, >—CH₂, N(CH₂CH₂)₂N—CH), 4.04 (1H, s, CH—N), 5.88 (2H, s, OCH₂—), 6.28 (1H, s, CH=C), 6.66 (1H, s, arom.), 7.02 (1H, s, arom.) | 2920, 1460, 1320, 1175, 1035, 860 |
| 19b | .HCl | | 2950, 2700–2100, 1475, 1330, 1035, 930 |
| 20a | | 0.88–1.08 (3H, m, —CH₃), 1.24–1.76 (4H, m, —CH₂CH₂—), 2.30–2.92 (12H, m, >—CH, N(CH₂CH₂)₂N—CH₂—), 3.10 (1H, s, OH), 3.66 (2H, t, J=6Hz, CH₂OH), 4.12 (1H, s, CH—N), 6.02 (2H, s, OCH₂—), 6.40 (1H, s, CH=C), 6.78 (1H, s, arom.), 7.12 (1H, s, arom.) | 3400, 2920, 2825, 1460, 1320, 1030, 930 |
| 20b | .HCl | | 3350, 2920, 2700–2100, 1470, 1320, 1230, 1025 |
| 21a | | 0.88–1.04 (3H, m, —CH₃), 1.24–1.88 (6H, m, —CH₂CH₂—, N—CH₂CH₂CH₂N), 2.18 (3H, s, CH₃—N), 2.24 (6H, s, N(CH₃)₂), 2.20–2.74 (6H, NCH₂CH₂CH₂N, >—CH₂—), 4.14 (1H, s, CH—N), 6.00 (2H, s, O—CH₂), 6.36 (1H, s, CH=C), 6.76 (1H, s, arom.), 7.08 (1H, s, arom.) | 2930, 1460, 1315, 1035, 860 |
| 21b | .HCl | | 2925, 2750–220, 1470, 1330, 1030 |
| 22a | | 0.88–1.04 (3H, m, —CH₃), 1.02 (6H, t, J=8Hz, N—(CH₂CH₃)₂), 1.24–1.74 (4H, m, —CH₂CH₂—), 2.24–2.86 (10H, m, >—CH—, N—CH₂CH₂—N(CH₂CH₂)), 2.28 (3H, s, N—CH₃), 4.16 (1H, s, CH—N), 6.02 (2H, s, OCH₂), 6.40 (1H, s, CH=C), 6.78 (1H, s, arom.), 7.14 (1H, s, arom.) | 2955, 1460, 1320, 1040, 940, 860 |
| 22b | .HCl | | 2920, 2750–2100, 1470 1320, 1030 |
| 23a | | 0.86–1.04 (3H, m, —CH₃), 1.20–1.76 (10H, —CH₂CH₂—, N(CH₂CH₂)₂CH₂), 2.24 (3H, s, CH₃—N), 2.24–2.88 (10H, >—CH₂—, N—CH₂CH₂N(CH₂CH₂)), 4.10 (1H, s, CH—N), 5.92 (2H, s, OCH₂), 6.30 (1H, s, CH=C), 6.70 (1H, s, arom.), 7.02 (1H, s, arom.) | 2930, 1465, 1320, 1040, 865 |
| 23b | .HCl | | 2920, 2750–2100, 1470, 1320, 1030 |

TABLE 2-2-continued

| Example | Compound (see, Table 2-1) | NMR (CDCl$_3$) δ | IR $v_{max}^{neat}$ or $KBr$ cm$^{-1}$ |
|---|---|---|---|
| 24a | | 0.84 (6H, d, J=6Hz, —CH(CH$_3$)$_2$), 0.88–1.04 (3H, m, —CH$_3$), 1.14–1.84 (5H, m, —CH, —CH$_2$CH$_2$—), 2.04 (2H, d, J=7Hz, N—CH$_2$—), 2.20–2.84 (10H, m, >—CH$_2$—, N(piperazine)N—), 4.02 (1H, s, CH—N), 5.90 (2H, s, OCH$_2$), 6.28 (1H, s, CH=C), 6.66 (1H, s, arom.), 7.04 (1H, s, arom.) | 2925, 1460, 1320, 1150, 1035, 940, 860 |
| 24b | .HCl | | 2950, 2700–2100, 1470, 1320, 1030, 930 |
| 25a | | 0.88–1.04 (3H, m, —CH$_3$), 1.04 (3H, t, J=8Hz, NCH$_2$C$\underline{H}_3$), 1.10–1.90 (6H, m, —CH$_2$CH$_2$—, NCH$_2$C$\underline{H}_2$CH$_2$N), 2.30–2.94 (12H, >—CH$_2$, N(CH$_2$CH$_2$CH$_2$, CH$_2$CH$_2$)N—C$\underline{H}_2$), 4.06 (1H, s, CH—N), 5.90 (2H, s, OCH$_2$), 6.26 (1H, s, CH=C), 6.66 (1H, s, arom.), 7.00 (1H, s, arom.) | 2925, 1460, 1310, 1120, 1035, 935, 860 |
| 25b | .HCl | | 2920, 2700–2100, 1470, 1320, 1030, 930 |
| 26a | | 0.80–1.08 (6H, m, —CH$_3$, —CH$_3$), 1.18–1.76 (8H, m, —CH$_2$CH$_2$—, —CH$_2$CH$_2$—), 2.18–2.88 (12H, >—CH$_2$, N(piperazine)N—CH$_2$—), 4.02 (1H, s, CH—N), 5.88 (2H, s, OCH$_2$—), 6.26 (1H, s, CH=C), 6.64 (1H, s, arom.), 7.00 (1H, s, arom.) | 2925, 1460, 1320, 1150, 1035, 860 |
| 26b | .HCl | | 2920, 2700–2100, 1470, 1320, 1025, 920 |
| 27a | (diastereomer mixture) | 0.88–1.04 (3H, m, —CH$_3$), 1.30 (6H, d, J=7Hz, —CH(CH$_3$)$_2$), 1.20–1.76 (4H, m, —CH$_2$CH$_2$—), 2.28–2.92 (17H, >—CH$_2$—, N—CH$_2$CH$_2$—N(piperazine)N—CH$_2$, OH), 2.32 (3H, s, CH$_3$—N), 3.40 (1H, m, J=7Hz, —CH<), 4.16 (1H, s, CH—N), 4.68–4.86 (1H, m, —C$\underline{H}$—OH), 6.00 (2H, s, OCH$_2$—), 6.36 (1H, s, CH=C), 6.76 (1H, s, arom.), 7.08 (1H, s, arom.), 7.32–7.54 (5H, m, arom.) | 3400, 2925, 1460, 1310, 1150, 1035, 755 |
| 27b | (diastereomer mixture) .HCl | | 3350, 2950, 2700–2100, 1470, 1320, 1030 |
| 28a | | 0.94 (3H, t, J=8Hz, CH$_2$CH$_2$C$\underline{H}_3$), 1.02 (3H, t, J=8Hz, N—CH$_2$C$\underline{H}_3$), 1.36–1.80 (2H, m, CH$_2$C$\underline{H}_2$CH$_3$), 2.20–2.80 (12H, m, N(CH$_2$CH$_2$, CH$_2$CH$_2$)N—CH$_2$, >—CH$_2$), 4.00 (1H, s, CH—N), 5.83 (2H, s, OCH$_2$O), 6.22 (1H, s, PhCH=C), 6.60 (1H, s, arom.), 6.96 (1H, s, arom.) | 2925, 1465, 1320, 1035, 730 |
| 28b | .HCl | | 2950, 2700–2100, 1470, 1320, 1030 |

Having now fully described the invention, it will be apparent to one of the ordinary skill in the art that many changes and modifications can be made thereto without departing from the spirit or scope of the invention as set forth herein.

What is claimed as new and is secured by letters patent:

1. An indene compound of the formula (I):

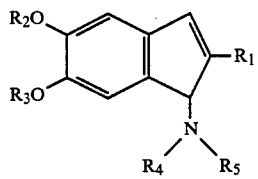

wherein $R_1$ is a lower alkyl group, $R_2$ and $R_3$ are, individually, a lower alkyl group or, in combination, are an alkylenedioxy group, and $R_4$ and $R_5$ are, individually, phenyl or benzyl, or a lower alkyl group which is substituted with a di(lower alkyl) amino group, and salts thereof.

2. The indene compound of claim 1, wherein $R_4$ and $R_5$ are $C_{1-4}$ alkyl groups.

3. The indene compound of claim 2, wherein $R_4$ and $R_5$ are methyl, ethyl or n-butyl groups.

4. The indene compound of claim 1, wherein $R_4$ and $R_5$ are, individually, a phenyl or benzyl group.

5. The indene compound of claim 1, wherein $R_4$ and $R_5$ are, individually, a lower alkyl group substituted with a di(lower alkyl)amino group.

6. The indene compound of claim 5, wherein said di(lower alkyl)amino group is a dimethyl or diethyl amino group.

7. The indene compound of claim 5, wherein $R_4$ and $R_5$ are, individually, selected from the group consisting of dimethylaminoethyl, 3-dimethylaminopropyl and diethylaminoethyl groups.

8. The indene compound of claim 1, wherein said salt is an inorganic salt.

9. The indene compound of claim 8, wherein said salt is selected from the group consisting of hydrochlorides, hydrobromides and hydroperchlorides.

10. The indene compound of claim 1, wherein said salt is an organic salt.

11. The indene compound of claim 10, wherein said salt is selected from the group consisting of fumarates, succinates, tartrates, maleates and oxalates.

12. An indene compound of the formula (I):

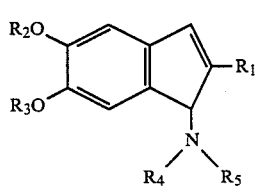

wherein $R_1$ is a lower alkyl group, $R_2$ and $R_3$ are, individually, a lower alkyl group or, in combination, are an alkylenedioxy group, and $R_4$ and $R_5$, individually, are selected from the group consisting of 4-[2-(1,3-benzothiazolyl)]benzyl, 2-(4-isopropylthiophenyl)-2-hydroxyethyl, 2-[4-(2-furanylcarbonyl)-1-piperazinyl]ethyl, 2-piperidinoethyl and 2-[4-[2-(4-isopropylthiophenyl)-2-hydroxyethyl]-1-piperazinyl]-ethyl groups, and salts thereof.

13. The indene compound of claim 12, wherein said salt is an inorganic salt.

14. The indene compound of claim 13, wherein said salt is selected from the group consisting of hydrochlorides, hydrobromides and hydroperchlorides.

15. The indene compound of claim 12, wherein said salt is an organic salt.

16. The indene compound of claim 15, wherein said salt is selected from the group consisting of fumarates, succinates, tartrates, maleates and oxalates.

* * * * *